United States Patent [19]

Ross et al.

[11] 4,064,241

[45] Dec. 20, 1977

[54] 7[(CARBOXYOXIRAN-3-CARBOXAMIDO)-PHENYLACETAMIDO]CEPHALOSPORIN DERIVATIVES

[75] Inventors: Barry Clive Ross, Birchington; Braham Shroot, Canterbury, both of England

[73] Assignee: Pfizer Inc., New York, N.Y.

[21] Appl. No.: 628,543

[22] Filed: Nov. 3, 1975

[30] Foreign Application Priority Data

Nov. 7, 1974 United Kingdom .................... 48116

[51] Int. Cl.$^2$ .................... A61K 31/545; C07D 501/36
[52] U.S. Cl. .................... 424/246; 260/281 R; 260/346.3; 260/347.3; 260/347.5; 260/348.62; 260/348.55; 260/348.51; 260/348.46; 260/333; 544/27; 260/345.7 R; 260/345.8 R
[58] Field of Search .................... 260/243 C; 424/246

[56] References Cited

U.S. PATENT DOCUMENTS

| 3,341,532 | 9/1967 | Lewis et al. .................... 260/243 C |
| 4,016,158 | 4/1977 | Martel et al. .................... 260/243 C |

FOREIGN PATENT DOCUMENTS 2,126,277  6/1970  Germany .................... 260/243 C

*Primary Examiner*—Nicholas S. Rizzo
*Assistant Examiner*—David E. Wheeler
*Attorney, Agent, or Firm*—Connolly and Hutz

[57] ABSTRACT

A series of novel 7-(D-α-acylaminoarylacetamido)-Δ$^3$-cephem derivatives have been prepared wherein the acyl moiety contains an epoxy group immediately adjacent to the carbonyl carbon atom. These compounds are useful as antibacterial agents for the treatment of diseases caused by Gram-negative and Gram-positive bacteria. Preferred members include 7-[D-α-(cis-2-carboxyoxiran-3-carboxamido)phenylacetamido]-3-(1-methyl-1,2,3,4-tetrazol-5-ylthiomethyl)-Δ$^3$-cephem-4-carboxylic acid and 7-[Dα-(cis-2-carboxyoxiran-3-carboxamido)phenylacetamido]cephalosporanic acid. Alternate methods of preparation are provided for these compounds and the principal synthetic route is described in detail.

10 Claims, No Drawings

7[(CARBOXYOXIRAN-3-CARBOXAMIDO)-PHENYLACETAMIDO]CEPHALOSPORIN DERIVATIVES

BACKGROUND OF THE INVENTION

This invention relates to new and useful antibacterial agents. More specifically, it is concerned with a novel class of cephalosporin derivatives which posses broad-spectrum antibacterial activity, especially against the Gram-negative microorganisms. In particular, the compounds, of the invention constitute a series of 7-(α-aminoarylacetamido)-Δ³-cephem derivatives with a novel type of acryl moiety attached to the α-amino group.

In the past, various attempts have been made by numerous investigators in the field of chemotherapy to obtain new and better antibacterial agents. For the most part, these efforts have involved the synthesis and testing of various new and heretofore unavailable organic compounds, particular in the area of semi-synthetic antibiotics like the cephalosporin derivatives. For instance, D.A. Cox et al. in Belgian Pat. No. 819,798 disclose various 7-(D-α-acylaminoarylacetamido)cephalosporanic acid derivatives useful for these purpose. However, in the search for still new and more improved antibacterial agents, little is known about the effect of an epoxy linkage on compounds of this type and particularly, an epoxy group directly attached to the carbonyl carbon atom of the aforesaid acylamino moiety of which it forms a part.

SUMMARY OF THE INVENTION

According to the present invention, there are provided novel compounds having the general formula:

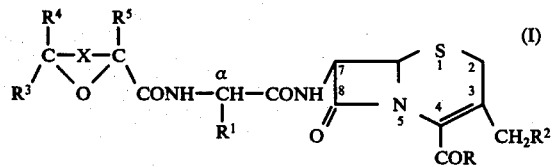

and the pharaceutically acceptable base salts thereof, wherein $R^1$ is a member selected from the group consisting of phenyl, thienyl and 2-furyl, and substituted phenyl wherein the substituent is chosen from the group consisting of halogen, hydroxy, lower alkyl, lower alkoxy and trifluoromethyl; R is hydroxy, and $R^2$ is a member selected from the group consisting of hydrogen, hydroxy, acetoxy, carbamoyloxy, N-pyridyl and substituted N-pyridyl, azido, pyrimidin-2-ylthio, 4,6-dimethylpyrimidin-2-ylthio, 4,5-dimethylthiazol-2-ylthio, 1,3,5-triazin-2-ylthio, 2-methyl-1,3,4-thiadizol-5-ylthio, 2-methyl-1,3,4-oxadiazol-5-ylthio and 1-substituted-1,2,3,4-tetrazol-5-ylthio wherein the 1-substituent is chosen from the group consisting of lower alkyl, benzyl, phenyl, chlorophenyl and anisyl, and R and $R^2$ when taken together represent an oxygen atom; $R^3$ is a member selected from the group consisting of carboxy, $COOR^6$ wherein $R^6$ is chosen from the group consisting of lower alkyl, 5-indanyl, naphthyl, phenyl and substituted phenyl wherein the substituent is chosen from the group consisting of halogen, lower alkyl, lower alkoxy and trifluoromethyl, and $CONR^7R^8$ wherein $R^7$ and $R^8$ are each chosen from the group consisting of hydrogen, lower alkyl and cycloalkyl having from three to six carbon atoms; X is a member selected from the group consisting of $-(CH_2)_2-$, $-(CH_2)_3-$, $-CH=CH-$ and a direct carbon-carbon link; and $R^4$ and $R^5$ are each a member selected from the group consisting of hydrogen and lower alkyl, and when X is a direct link, $R^4$ and $R^5$ taken together complete a ring chosen from the group consistng of cyclopentyl and cyclohexyl.

The pharmaceutically acceptable base salts of the novel compounds of the invention are all derived from pharmacologically acceptable cations and they include non-toxic metallic salts, particularly of lithium, sodium, potassium, calcium and aluminum, as well as ammonium and substituted ammonium salts, such as salts of trialkylamines, N-ethylpiperidine, procaine, dibenzylamine, N-benzyl-β-phenylethylamine, 1-ephenamine, N,N'-dibenzylethylenediamine, dehydroabietylamine, N,N'-bis-dehydroabiethylenediamine and other amines previously used to form salts with benzylpenicillin. Compounds of the formula (I) in which R is a hydroxy group and $R^2$ represents an N-pyridyl moiety, itself positively charged, are internal salts, having the 4-carboxyl group converted to the corresponding carboxy anion, $COO^-$. In the case of all the aforementioned normal salts, a single cation may accompany the terminal deprotonated carboxyl group represented by $R^3$ or the deprotonated 4-carboxy group repesented by R, or else there may be two cations, one accompanying each of the two deprotonated groups.

In this specification, it is to be understood that by the use of the term "lower" before alkyl and alkoxy, we mean those such groups which contain up to six carbon atoms (and preferably, up to four carbon atoms), while "halogend" is defined as simply being fluorine, chlorine, bromine or iodine. In the case of those alkyl and alkoxy groups which contain more than three carbon atoms, the carbon chain may either be straight or branched.

One preferred group of compounds of the present invention are those of the formula (I) in which R is hydroxy, $R^1$ is phenyl, $R^2$ is hydrogen, acetoxy or 1-(lower alkyl)-1,2,3,4-tetrazol-5-ylthiomethyl; $R^3$ is carboxy or $COOR^6$ wherein $R^6$ is either phenyl or lower alkoxyphenyl, and X is either $-(CH_2)_2-$, $-CH=CH$ or a direct carbon-carbon link, and $R^4$ and $R^5$ taken together complete a cyclohexyl ring.

The most preferred group of compounds of the present invention are those of the formula (I) in which R is hydroxy, $R^1$ is phenyl, $R^2$ is hydrogen, acetoxy or a 1-methyl-1,2,3,4-tetrazol-5-ylthio, $R^3$ is carboxy, $R^4$ and $R^5$ are each hydrogen or methyl and X is a direct carbon-carbon link. Typical member compounds of the most preferred class include such compounds as 7-[D-α-(cis-2-carboxyoxiran-3-carboxamido)-phenylacetamido]-3-(1-methyl-1,2,3,4-tetrazol-5-ylthiomethyl)-Δ³-cephem-4-carboxylic acid and 7-[D-α-(cis-2-carboxyoxiran-3-carboxamido)phenylacetamido]-cephalosporanic acid, respectively.

The cephalosporin derivatives of the present invention are capable of existing in epimeric D- and L- forms, and the invention includes the separated D- and L-epimers as well as racemic DL-mixtures thereof as all being well within the scope.

The invention also includes within its scope various novel pharmaceutical compositions comprising a compound of the formula (I) together with a pharmaceutically acceptable carrier or diluent, and it additionally provides a method for treating an animal of diseases caused by either Gram-negative or Gram-positive bacteria by administering to said animal an antibacterially-effective amount of a compound of the formula (I) or a pharmaceutical composition thereof as hereinbefore defined

DETAILED DESCRIPTION OF THE INVENTION

The compounds of the invention may be prepared in a number of ways, including the following:

1. Compounds of the formula (I), in which $R^3$ is a carboxyl group and $R^2$ is as defined for formula (I) other than hydroxy can be prepared by reacting a 7-(α-aminoarylacetamido)-Δ$^3$-cephem derivative of the formula:

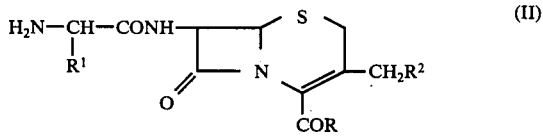

wherein $R^2$ is defined above in this method, with a cyclic anhydride of the formula:

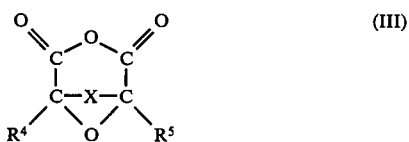

This particular reaction is normally accomplished by mixing the two reagents together, using compound of formula (II) optionally as a salt or necessarily as an internal salt in the case where $R^2$ represents an N-pyridyl group and R is a hydroxy group, in a reaction-inert organic solvent medium, e.g., dimethylformamide, methylene chloride or acetone, optionally containing a tertiary amine base, e.g., triethylamine or pyridine, or an inorganic base, e.g., sodium bicarbonate. Generally speaking, the reaction is substantially complete within a period of from about one-half to about 12 hours when the mixture is maintained at a temperature within the range of from about 0° C. to about 45° C., preferably with stirring. Isolation of the desired product is typically achieved by extracting the reaction mixture with a basic aqueous medium such as saturated aqueous sodium bicarbonate solution, separating and acidifying the aqueous phase to a low pH value (e.g., pH 1.0) by adding, for example, a mineral acid such as hydrochloric acid, and extracting the resulting aqueous acidified solution with a water-immiscible organic solvent (e.g., ethyl acetate) in order to extract the product into the organic phase, and thereafter separating, drying (e.g., with anhydrous magnesium or sodium sulfate), filtering and finally evaporating the aforesaid organic phase to dryness. If deemed necessary, the product may then be further purified by a standard recrystallization technique.

Inasmuch as this particular method employed a cyclic anhydride as starting material, i.e., a compound in which the carbonyl groups are in the cis configuration, only compounds of the formula (I) in which $R^3$ is a carboxyl group cis to the carbonyl group immediate adjacent to the oxygen-containing ring may be prepared from them. In other words, this particular method prepares compounds of the following type structure:

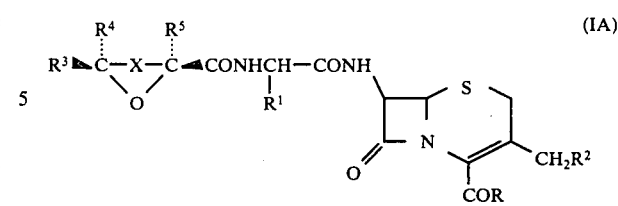

It should be noted, however, that compounds of the formula (I) in which X is a direct link and $R^4$ and $R^5$ when taken together represent a tri- or tetramethylene group only exist in the cis configuration.

When $R^4$ and $R^5$ in the compound of the formula (III) are different, a mixture of compounds of the formula (I) may be produced. For example, if $R^4$ in structural formula (III) is hydrogen and $R^5$ is methyl, the product may be mixture of two compounds, viz., (a) a compound of the formula (I) in which $R^4$ is hydrogen and $R^5$ is methyl, and (b) a compound of the formula (I) in which $R^4$ is methyl and $R^5$ is hydrogen. The compounds of the mixture may be separated, if necessary, by means of ion-exchange techniques well-known to those skilled in the art.

The anhydride starting materials of the formula (III) wherein X is a direct link may generally be prepared via the following reaction scheme:

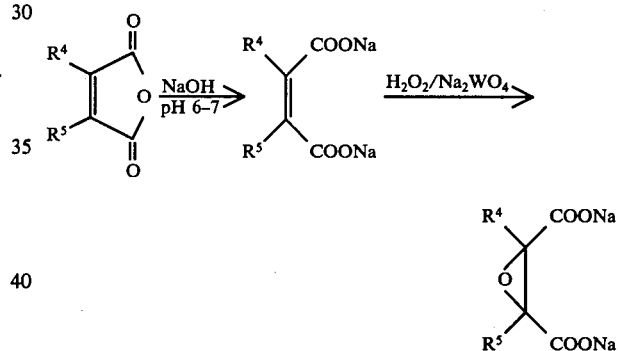

followed by conversion of the epoxy salt into the free acid and its subsequent conversion into the corresponding anhydride. The preparation of the epoxy salt in which $R^4$ and $R^5$ are both hydrogen is, in fact, described by Payne and Williams in the *Journal of Organic Chemistry*, Vol. 24, p. 54 (1959). The first step of this scheme is generally carried out by dissolving the unsaturated anhydride in an equivalent amount of aqueous sodium hydroxide solution, employing a gentle heating of the solution if necessary. Hydrogen peroxide and a catalytic amount of sodium tungstate ($Na_2WO_4$) are then added to the reaction mixture, which is generally maintained at a temperature ranging from about 50° C. up to about 70° C. and at a pH value in the range of about pH 4–6, in order to expodize the double bond. The reaction is normally exothermic and thus, only initial heating may be required. The epoxidized salt may then be converted into the free acid by conventional techniques as hereinafter described.

Thus, for example, when the desired epoxy acid is insoluble or only partially soluble in water, the solution of the epoxy salt may be acidified with a mineral acid such as hydrochloric acid, followed by extraction of the so-produced epoxy acid into diethyl ether, drying the ether and evaporating the dry etheral solution in vacuo to afford the desired acid.

When the desired epoxy acid is very soluble in water, it is generally necessary to isolate the epoxy salt prior to converting it into its acid form, for example, by evaporating the solution to approximaely one-half its original volume and pouring it into a large excess of a solvent in which the salt is insoluble, e.g., acetone, thereby precipitating the salt. The isolated epoxy salt may then be converted into its acid form by passing it through a cation-exchange resin in the acid form. A suitable cation-exchange resin in this connection is "Bio-Rad" AG 50W-X4 in its acid form (the latter is the registered trademark name of Bio-Rad Laboratories of Richmond, California for a polystyrene sulfonic acid type resin). In the case where $R^4$ and $R^5$ are both hydrogen or both methyl, it has been found that the isolated epoxy salt may also be converted into its acid form by mixing an aqueous solution of said salt with hot aqueous solution of barium chloride so as to convert the sodium salt to the barium salt, with the barium salt precipitating on cooling. The barium salt may then be dried, and the dry barium salt together with anhydrous magnesium sulfate thereafter suspended in a dry diethyl ether to which there is added an ethereal solution of pure sulfuric acid, with the temperature of the reaction solution being maintained in the range of from about 0° C. to about 10° C. throughout the addition step. After stirring for several hours, the solution is filtered and then evaporated to dryness to leave the desired epoxy acid.

The epoxy acids may then be converted to their corresponding anhydrides of the formula (III) by reacting an ethereal solution of the acid with an ethereal solution of dicyclohexylcarbodiimide at room temperature (~25° C.) for a period of time up to about an hour. Other solvents, such as methylene chloride, may be used as alternatives or in addition to diethyl ether, provided they are capable of dissolving the epoxy acid. After the filtration step, the solution may be evaporated in vacuo to leave the desired anhydride.

The preparation starting materials of the formula (III) wherein X is other than a direct link may be generally carried out by reacting an ethereal solution of an acid of the formula

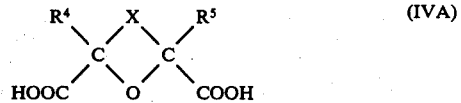

(IVA)

wherein x is —$(CH_2)_2$—, —$(CH_2)_3$— or —CH=CH— and the carboxyl groups are in the cis configuration, with an ethereal solution of dicyclohexylcarbodiimide at room temperature for a period of up to about an hour. Following filtration, the solution may be evaporated in vacuo to leave the anhydride. The cis-acids of the formula (IVA) are either known compounds or may be prepared by methods similar to those described in the prior art.

2. Compounds of the formula (I) in which $R^2$ is as defined for formula (I) other than hydroxy, $R^3$ is a carboxyl group trans to the carbonyl group immediately adjacent to the oxygen-containing ring, and $R^4$ and $R^5$ are as defined for formula (I) other than tri- or tetramethylene, can be prepared by reacting an acid of the formula:

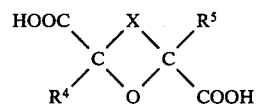

(IVB)

wherein $R^4$ and $R^5$ are as defined in this method and X is as defined in formula (I), with the dehydrating agent, e.g., dicyclohexylcarbodiimide, to produce a polymeric anhydride, and the polymeric anhydride is then reacted with a compound of the formula (II) in which $R^2$ is other than hydroxy.

Typically, a solution of the acid in an inert solvent such as diethyl ether or dichloromethane is reacted with a solution of dicyclohexylcarbodiimide in the same solvent. Generally, this reaction may be carried out at room temperature for a period of time of no more than about one hour. The polymeric anhydride is then mixed with a compound of the formula (II), optionally as a salt or necessarily as an internal salt in the case where $R^2$ is an N-pyridyl group and R is a hydroxy group, in a reaction-inert organic solvent, e.g., dimethylformamide, methylene chloride or acetone, optionally containing a tertiary amine base, e.g., triethylamine or pyridine, or an inorganic base, e.g., sodium bicarbonate. The reaction generally goes substantially to completion in a period of from about one-half to about 12 hours when the mixture is maintained at a temperature within the range of from about 0° C. to about 45° C., preferably with stirring. The reaction mixture is then extracted with a basic aqueous medium such as saturated aqueous sodium bicarbonate solution, and the aqueous phase is then acidified to a low pH value, e.g., pH 1.0, by the addition of a mineral acid thereof, e.g., hydrochloric acid, to produce the desired compound of the formula (I). The product may be recovered by extracting the aqueous acidified solution with a water-immersicible organic solvent, e.g., ethyl acetate, in order to extract the product into the organic phase, and thereafter separating, drying (e.g., with anhydrous magnesium or sodium sulfate), filtering and evaporating the organic phase dryness. If necessary, the trans-product may subsequently be further purified by standard recrystallization techniques.

The trans-acid starting materials for this method are either known compounds or may be prepared by methods analogous to those of the prior art. For example, the trans-acid starting materials wherein X is a direct link may be prepared by the following scheme [see *Journal of Organic Chemistry*, Vol. 124, p. 54 (1959) and *Journal of the Chemical Society* (London), p. 118 (1962)]:

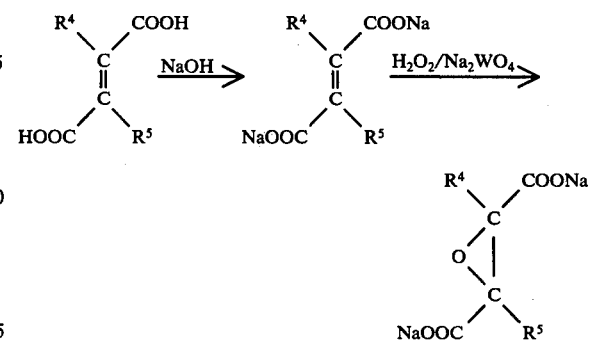

The reaction conditions for the above scheme may be the same as those for the related scheme of method (1)

above, the trans-epoxy salt being converted into its acid form by cation-exchange techniques. As previously indicated, compounds of the formula (I) in which R⁴ and R⁵ when taken together represent a tri- or tetramethylene group do not exist in the trans configuration.

3. A half-ester of the formula:

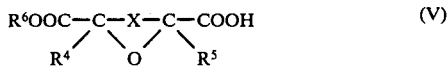

wherein R⁴, R⁵, R⁶ and X are as defined for formula (I), and which itself may be prepared according to conventional procedures, e.g., by reacting the appropriate compound of the formula (III) with a lower alkanol R⁶OH in the presene of a tertiary base or with the sodio derivative of a lower alkanol, phenol, substituted phenol, 5-indanol or naphthol, R⁶ONa, followed by acidification, can also be reacted as such or after its conversion to the corresponding acid chloride, or an "activated" ester or mixed anhydride, with a 7-(α-aminoarylacetamido)-Δ³-cephem derivative of the formula (II) in which R² is other than hydroxy to form a compound of the formula (I) in which R³ is an ester group, COOR⁶ as hereinbefore defined and R² is as defined for formula (I) other than hydroxy. Since the carbonyl groups of the half-esters produced by the above technique will be in the cis configuration, only compounds of the formula (I) in which R³ is the group —COOR⁶ cis to the carbonyl group immediately adjacent to the oxygen-containing ring may be prepared from them.

If, on the other hand, the trans-product is required, a half-ester of the formula (V) in which R⁴ and R⁵ are other than tri- or tetramethylene and the carbonyl groups are in the trans configuration must be used, and this ester may be prepared by reacting the corresponding trans-dicaarboxylic acid with one equivalent of an alkanol of the formula R⁶OH under conventional esterification conditions. This procedure, however, is not applicable when R⁴ and R⁵ when taken together represent tri- or tetramethylene because the dicarboxylic acid starting material can only be obtained in the cis-form.

If the half-ester is to be reacted as such, this step is conveniently effected in the presence of a dehydrating agent, e.g., dicyclohexylcarbodiimide or carbonyl-diimidazole. In a typical procedure using carbonyl-diimidazole, a solution of the half-ester in a suitable reaction-inert organic solvent, e.g., methylene chloride, is added to a cooled solution of the dehydrating agent in the same solvent and after evolution of carbon dioxide has ceased, the mixture is stirred at room temperature for a short time prior to addition of the Δ³-cephem derivative. The reaction may then be allowed to proceed for several hours at room temperature, preferably with continual stirring of the solution. Isolation of the desired product therefrom may then be effected by evaporation of said solution to dryness while under reduced pressure, followed by dissolution of the residue in water and extraction of the acidified aqueous solution into a water-immiscible organic solvent, e.g., ethyl acetate, and subsequent evaporation of the optionally washed and dried (e.g., with anhydrous magnesium sulfate) organic phase to near dryness. The crude product thus produced may then be further purified, suitably by using a standard crystallization technique, etc.

The same reaction may alternatively be performed in aqueous solution using a water-soluble diimide as the dehydrating agent, of which a typical example is 1-(3-dimethylamino-n-propyl)-1-ethylcarbodiimide hydrochloride. In such a case, a mixture of the two reagents and the water-soluble diimide is added to an aqueous solvent, e.g., water itself or aqueous acetone, and the pH of the resulting solution is adjusted to pH 5–6, e.g., by adding hydrochloric acid, and thereafter maintained within that acidity range for several hours until stabilization is effected, i.e., when no further quantity of mineral acid is required to maintain the pH within the aforesaid acidity range. The product may then be extracted into a water-immiscible organic solvent, e.g., ethyl acetate, after first acidifying the aqueous phase further, e.g., to pH 2, and isolated as such by evaporting to dryness the optionally washed and dried organic phase. Further purification may then be effected by suitable means.

If it is desired to react the half-ester of the formula (V) as its acid chloride with the 7-(α-aminoarylacetamido)-Δ³-cephem derivative, the initial conversion step to the acid chloride may be effected using a well-known standard technique for such a reaction, viz., by maintaining a solution of the half-ester and a chlorinating agent such as oxalyl chloride or thionyl chloride in a suitable reaction-inert organic solvent, e.g., benzene, for several hours, preferably with stirring, at a suitable temperature, and isolating the crude product therefrom by evaporating the thus obtained reaction solution to dryness. Thereafter, the residue is conveniently reacted directly with the appropriate Δ³-cephem derivative, without purification, in an appropriate solvent, e.g, aqueous acetone, containing a base of the type exemplified in method (1) above. After allowing a sufficient reaction time, e.g., several hours, the product is conveniently isolated and then purified by extracting it from an acidified aqueous solution of low pH value into an organic phase, e.g., ethyl acetate, and then following a similar procedure to that described in the aforesaid method (1) for the isolation and purification of the product.

The half-ester of the formula (V) may be converted into an "activated" ester prior to reaction with the 7-(α-aminoaryl-acetamido)-Δ³-cephem derivative, using the preferred reagent N-hydroxy-succinimide in the presence of a dehydrating agent such as dicyclohexylcarbodiimide. The "activated" ester product of the formula:

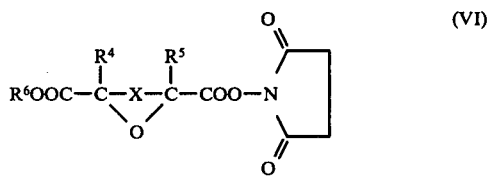

is then conveniently reacted wiht the Δ³³-cephem derivative in the reaction solution in which it is formed, without any prior isolation being necessary. In a typical pocedure, a solution of the half-ester, N-hydroxy-succinimide and a dehydrating agent in a reaction-inert organic solvent, e.g., tetrahydrofuran, is stirred for several hours at room temperature, after which the solid N,N'-dicyclohexylurea formed in the reaction is removed, preferably by means of filtration. To the solution containing the "activated" ester, there is then added a solution of the Δ³-cephem derivative, and the reaction equilibrium generally shifts substantially to completion in the presence of a tertiary amine or inorganic base, as hereinbefore exemplified and preferably with stirring during a period from about one to about 12 hours at room temperature. The solvent may then be removed, e.g., by means of evaporation in vacuo, and the residue dissolved in water, with the aqueous solution then being acidified to a low pH value and subsequently extracted with a water-immiscible organic solvent, e.g., ethyl acetate. The resultant organic phase is then subjected to a procedure similar to that described in method (1) for the isolation and purification of the product.

If the half-ester of the formula (V) is to be converted to a mixed anhydride of the formula (VII), as hereinafter illustrated, prior to reaction with the 7-($\alpha$-aminoarylacetamido)-$\Delta^3$-cephem derivative, the initial conversion step is suitably performed by using a lower alkyl chloroformate such as ethyl chloroformate. The reaction may be suitably effected by stirring a mixture of the half-ester, lower alky chloroformate and an equivalent amount of a tertiary amine or inorganic base of the type hereinbefore exemplified, in a suitable solvent, e.g., methylene chloride, at a low temperature, e.g., 0° C., for a short time period, e.g., ½ hour. Reaction with the $\Delta^3$-cephem derivative may then be effected, without the necessity of isolating the mixed anhydride, by adding a solution of said derivative in a suitable solvent, e.g., methylene chloride, containing an equivalent amount in moles of a base of the type hereinbefore exemplified, to the reaction solution of the mixed anhydride of the formula:

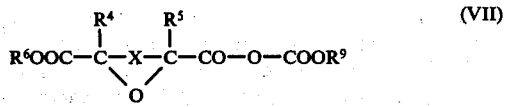

(VII)

wherein $R^9$ represents a lower alkyl group, and thereafter stirring the reaction solution at room temperature for several hours. Isolation and purification of the desired product may then be effected by removing the reaction solvent, e.g., by evaporation in vacuo, and dissolving the residue in water, followed by acidification of the aqueous solution and then extracting it with a water-immiscible organic solvent such as ethyl acetate. The resultant organic phase is then subjected to a procedure similar to that described in method (1) for the final stages.

4. Compounds of the formula (I) in which $R^3$ represents a carbamoyl group of the formula $CONR^7R^8$, as hereinbefore defined, are prepared by reacting a half-amide of the formula:

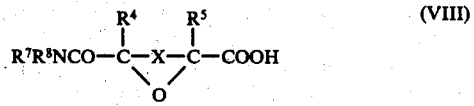

(VIII)

optionally after conversion to its acid chloride, "activated" ester or mixed anhydride, with a 7-($\alpha$-aminoarylacetamido)-$\Delta^3$-cephem derivative of the formula (II) in which $R^2$ is other than hydroxy. The half-amide of the formula (VIII) wherein the —CO— group are in the cis configuration may itself be prepared by reacting the appropriate amine, $R^7R^8NH$, with a cyclic acid anhydride of the formula (III) according to conventional procedure. The half-amide of the formula (VIII) wherein the —CO— groups are in the trans configuration and $R^4$ and $R^5$ are other than tri- or tetra-methylene may be prepared by reacting excess polymeric anhydride prepred in the first step of method (2) above with an amine of the formula $R^7R^8NH$.

The reaction between the half-amide or aforementioned derivative thereof and the $\Delta^3$-cephem derivative, as well as the conversion of the half-amide into the appropriate derivative prior to reaction with the $\Delta^3$-cephem derivative, may be achieved according to procedures analogous to those given in method (3), by merely starting from the appropriate half-amide rather than the half-ester. The appropriate isolation techniques may also be effected analogously.

5. Compounds of the formula (I) in which $R^2$ represents a substituted or unsubstituted N-pyridyl group, an azido group or a heterocyclic-thio group can be prepared from the corresponding compounds in which $R^2$ represents an acetoxy group (cephalosporanic acid derivatives) by means of a displacement reaction with the appropriate pyridine compound, an alkali metal azide or the appropriate heterocyclic thiol as the case may be.

In the cases of $R^2$ representing an azido or a heterocyclicthio group, the reaction may generally be performed by adding the appropriate alkali metal azide or heterocyclic thiol reagent to a solution of the corresponding cephalosporanic acid derivative in an aqueous buffer solution, e.g., phosphate buffer, at a pH between about 6 and 7.5, said solution also optionally containing a base, e.g., sodium bicarbonate, and then heating the reaction mixture together within the temperature range of from about 35° C. to about 70° C. for a period of about one to about 12 hours. The product may then be isolated by diluting the spent reaction mixture with water, overlayering the aqueous medium with a suitable water-immiscible organic solvent, e.g. ethyl acetate, and acidifying the aqueous phase, e.g., to pH 2.0, by adding sufficient hydrochloric acid thereto, thereby inducing extraction of the product into the organic phase, especially with additional shaking. The organic phase is thereafter separated, washed, e.g., with a saline solution, dried, e.g., with anhydrous magnesium sulfate, filtered and evaporated to dryness. Purification of the crude product, if necessary, may then be achieved by a standard recrystallization technique or else by washing with a suitable solvent, e.g., diethyl ether.

In the case of $R^2$ representing a N-pyridyl group, the reaction may be performed by first adding the appropriate pyridine compound, e.g., in 1 to 3 molar equivalents, and then potassium thiocyanate or iodide, e.g., in 1 to 10 molar equivalents, to a molar equivalent of the cephalosporanic acid derivative dissolved in water containing at least one molar equivalent amount of a base of the type hereinbefore exemplified. To this mixture, there is then added sufficient phosphoric acid until a pH value of about pH 6.0 is attained and the entire reaction mixture is then suitably heated at a temperature within the range of from from about 25° C. up to about 70° C. for a period from about 6 to about 48 hours. The product, either as the thiocyanate or iodide salt, may then be isolated by adjusting the pH of the solution to pH 2.0, e.g., by the addition of 2N hydrochloric acid and thereafter collecting the resulting precipitate by means of filtration. The betaine form of the product can then be easily obtained by well-documented standard ion-exchange techniques.

6. The compounds of the formula (I) in which $R^2$ is a hydroxy group can be prepared by the hydrolysis of the corresponding cephaloporin in which $R^2$ is an acetoxy group. Typically, hydrolysis may be carried out in aqueous media at a pH of from about 5 to 8, using either a wheat germ esterase or acetyl citrus esterase. The enzyme in aqueous solution is normally added to the sodium salt of the acetoxy-containing cephalosporin in water. The pH is then rapidly adjusted to the desired value. The hydrolysis reaction is then effected by keeping the mixture at a suitable temperature, preferably a temperature between 20° C. and 45° C., by the addition of aqueous alkali thereto until said hydrolysis is complete. Completion of the hydrolysis reaction can be determined in the usual manner, e.g., by titration with aqueous alkali or by chromatographic assay.

The hydrolysis products may be recovered by conventional methods. Typically, the reaction mixture is overlayed with a water-immiscible organic solvent, e.g., ethyl acetate, and the mixture is then cooled and the pH adjusted to a value of from about 1.5 to about 4.5. The insoluble protein is then removed by means of filtration. The separated organic layer is then underlayered with water and the pH re-adjusted to a value of from about 4.5 to about 8.5. The resulting aqueous extract can then be freeze-dried or else concentrated in vacuo, and the resultant sodium salt thereafter purified by recrystallization from a water-miscible organic solvent system and preferably, from a mixture of lower alcohols, e.g., methanol and isopropyl alcohol.

7. The compounds of the formula (I) in which R and $R^2$ when taken together represent an oxygen atom, i.e., cephalosporins containing a lactone grouping, can be prepared by treating the corresponding derivative in which R and $R^2$ are each hydroxy with a mineral acid, e.g, 2N hydrochloric acid. Typically, the reaction is carried out in an aqueous solution containing a water-miscible organic solvent, e.g., aqueous dioxan, at a temperature of preferably from about 5° C. to about 50° C. for a period of several hours, e.g., 0.5–48 hours. The solution may then be concentrated in vacuo, and the precipitated product subsequently removed by means of filtration or centrifugation.

8. Compounds of the formula (I) in which $R^2$ is a carbamoyloxy group can be prepared by reacting the corresponding cephalosporin, in which $R^2$ is a hydroxy group, with a conventional protecting agent so as to protect the carboxyl group in the 4-position of the cephem nucleus and if also present, the carboxyl group in the 7-side chain. This step is then followed by reacting the thus protected compound with either trichloroacetyl isocyanate or chlorosulfonyl isocyanate and thereafter by the subsequent removal of the protecting groups. A suitable protecting agent is diphenyldiazomethane, which may be reacted with the unprotected cephalosporin in an inert solvent, e.g., ethyl acetate, typically at a temperature of from about 10° C. to about 45° C. for a period of from about ½ to about 48 hours. The resultant mono- or diester may then be dissolved in an inert organic solvent, e.g., acetone, and next treated with trichloroacetyl isocyanate at a temperature of preferably from about 0° C. to about 50° C. to give the corresponding trichloroacetylcarbamoyloxymethyl derivative. Treatment of this derivative with acid, e.g., 0.1N hydrochloric acid, or chromatography on silica gel, then gives the mono- or bis-diphenyl methyl ester of the 3-carbamoyloxymethyl compound (depending on whether or not the 7-side chain of the starting material contained a free carboxyl group). The ester group or groups can then be removed in a conventional manner, e.g., by the use of trifluoroacetic acid and anisole at temperatures of up to about 50° C.

9. Salts of the compounds of the invention can be prepared, if desired, by standard techniques. For example, preparation of the sodium or potassium salt of a compound of the invention can be accomplished by dissolving the compound in a lower alkanol, e.g. methanol, cooling the resultant solution and then adding a solution of the appropriate alkali metal acetate in the same solvent to the stirred organic solution. The reaction is, in many cases, effected by maintaining the reaction mixture for several hours at room temperature, and the salt is then isolated by concentrating the reaction solution via partial evaporation in vacuo and then adding the resulting concentrate to a large volume of a suitable organic solvent, e.g., diethyl ether, thereby precipitating the salt. Purification can then be achieved by washing the salt in a suitable solvent, e.g., diethyl ether, and therafter drying said salt to constant weight, preferably in vacuo.

The activity of the compounds of the present invention as antibacterial agents is clearly ascertained by their in vitro evaluation. The latter step was carried out by first determining the minimum inhibitory concentration (M.I.C.) of the individual test compound in a suitable nutrient medium containing the desired microorganism. The minimum inhibitory concentration (M.I.C.) is the level at which growth of the particular microorganism failed to occur. In practice, agar (i.e., brain/heart infusion agar) plates, each having incorporated therein the test compound at a particular concentration, were inoculated with a standard number of cells of the test microorganism and each plate was thereafter incubated for 24 hours at 37° C. The plates were then observed for the presence or absence of the growth of bacteria and the appropriate M.I.C. value noted. Microorganisms used in such tests and against which the compounds of the present invention were active included strains of *Escherichia coli, Klebsiella pneumoniae, Proteus mirabilis, Pseudomonas aeruginosa, Staphylococcus aureus, Streptococcus pyogenes, Proteus vulgaris, Enterobacter aerogenes, Haemophilus influenzae* and *Neisseria gonorrhea.*

A selection of M.I.C. values for many of the compounds of the invention, as hereinafter exemplified, with respect to their activities against certain of the various strains of microorganisms mentioned above is given below in the following table for illustrative purposes:

| Example No. of Compound | Escherichia coli 51A266 | Pseudomonas aeruginosa 52A490 | Klebsiella pneumoniae 53A009 | Klebsiella pneumoniae 53A015 | Proteus mirabilis 57C015 | Proteus vulgaris 57C060 | Streptococcus pyogenes 02C203 |
|---|---|---|---|---|---|---|---|
| I | 1.66 | 3.1 | 0.4 | 0.8 | 0.4 | 0.4 | 0.4 |
| II* | 50 | 100 | 12.5 | 12.5 | 6.2 | 6.2 | 12.5 |
| III | 3.1 | 6.2 | 1.6 | 6.2 | 0.4 | 0.2 | 6.2 |
| IV | 50 | >100 | 6.2 | 3.1 | 3.1 | 3.1 | 6.2 |
| VII | 12.5 | 12.5 | 6.2 | 6.2 | 6.2 | 6.2 | — |
| X | 12.5 | 6.25 | 6.25 | 6.25 | 6.25 | 6.25 | — |
| XI* | 6.2 | 6.2 | 3.1 | 12.5 | 1.6 | 1.6 | 6.2 |
| XII* | 3.1 | 6.2 | 1.6 | 1.6 | 0.8 | 0.8 | 1.6 |

| Example No. of Compound | Escherichia coli 51A266 | Pseudomonas aeruginosa 52A490 | Klebsiella pneumoniae 53A009 | Klebsiella pneumoniae 53A015 | Proteus mirabilis 57C015 | Proteus vulgaris 57C060 | Streptococcus pyogenes 02C203 |
|---|---|---|---|---|---|---|---|
| XIV | 6.2 | 6.2 | 6.2 | 25 | 3.2 | 1.6 | 6.2 |

*The product tested was a mixture of the two compounds of the formula (I) prepared in the Example indicated.

The compounds of the invention can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules either alone or in admixture with excipients, or else in the form of elixirs or suspensions containing flavoring or coloring agents. They may also be injected parenterally, i.e., intravenously, intramuscularly or subcutaneously. For parenteral administration, they are best used in the form of a sterile aqueous solution which may contain other solutes, e.g., sufficient saline or glucose to make the solution isotonic.

The compounds of the invention can be administered to humans for the treatment of diseases caused by Gram-negative and Gram-positive bacteria. In general, the dosage level will be in the range of approximately 125 mg. to 1.0 g. of active compound per day, taken in 2 to 4 divided daily doses, when given to the average adult human patient (70 kg.) for the present purposes at hand. However, variations will necessarily occur depending upon the weight and condition of the subject being treated and the particular route of administration chosen.

This invention is further illustrated by the following Examples, together with the preparation of the necessary starting materials (and/or intermediates) when the latter are deemed novel. Thus, although the cis-dicarboxylic acids are used in the preparation of the anhydrides were in most cases known compounds, the acids used to prepare the anhydrides of Examples V-VI and Examples XII-XIV are novel, and their preparation is described in Preparations A and B, respectively. In like manner, the anhydride starting materials used in Examples were either known compounds or were prepared by the conventional technique of reacting the corresponding cis-dicarboxylic acid with dicyclohexlcarbodiimide. Preparation C illustrates the formation of the anhydride used in Examples VII-VIII by this tenhnique.

Preparation A

Sodium hydroxide (4.0 g., 0.1 mole) was dissolved in water (30 ml.) and 3,4,5,6-tetrahydrophthalic anhydride (7.6 g., 0.05 mole) was added thereto, the mixture being stirred until solution of the anhydride occurred. 1N Aqueous hydrochloric acid (10 ml.) was next added to the solution to reduce the pH to 6.5, with the solution thereafter being heated to 70° C. Sodium tungstate (0.35 g., 0.001 mole) was then added, followed by 30% hydrogen peroxide solution (7 ml., 0.06 mole). The resulting solution was then heated at 70° C. for 1 hour, cooled and subsequently acidified with concentrated hydrochloric acid, followed by filtration. The filtrate was extracted three times with diethyl ether. After separation of the aqueous layer, the combined ether fractions were dried over anhydrous magnesium sulfate, filtered and evaporated under reduced pressure to leave an oil which crystallized under high vacuum to a white hygroscopic solid. In this manner, there was ultimately obtained 6.1 g. of 1,2-epoxycyclohexane-cis-1,2-dicarboxylic acid, m.p. 103° C.

Preparation B

Dimethyl maleic anhydride (3.78 g., 0.03 mole) was dissolved in 2N aqueous sodium hydroxide solution (30 ml., 0.06 mole). Sodium tungstate (0.21 g.) was then added, followed by hydrogen peroxide solution (30%, 4.2 ml.). The resulting solution was then warmed to about 50° C., the temperature of the solution increasing to 65° C. with no extra heating due to the exothermic nature of the epoxidization reaction. The solution was maintained at 65° C. for 1 hour, evaporated under reduced pressure to about one-half volume, and poured into a large volume of acetone to produce a white solid which was filtered off and dried. The latter product, which was the disodium salt of cis-$\alpha,\beta$-dimethyl-$\alpha,\beta$-epoxysuccinic acid (5.7 g.), was dissolved in water (25 ml.). On cooling, a white crystalline precipitate of the corresponding barium salt formed, which was subsequently dried for 2 hours at 60° C. (yield, 7.4 g.). The barium salt (7.4 g.), together with anhydrous magnesium sulfate (1.5 g.), was then suspended in dry diethyl ether (35 ml.), the ethereal solution being maintained at a temperature of between 0° C. and 5° C., with stirring. A solution of pure, concentration sulfuric acid (2.3 g.) in dry diethyl ether (10 ml.) was next added dropwise, with the resulting solution being stirred for 1 hour at 5° -10° C. The mixture was then stirred overnight (~16 hours) at room temperature. The solution was then filtered, and the filtrate subsequently evaporated under reduced pressure to give a solid characterized by nuclear magnetic resonance spectroscopy to be the dihydrate of cis-$\alpha,\beta$-dimethyl-$\alpha,\beta$-epoxysuccinic acid. The product was finally dried over $P_2O_5$ under reduced pressure to afford pure anhydrous cis-$\alpha,\beta$-dimethyl-$\alpha,\beta$-epoxysuccinic acid (yield, 1.96 g.), characterized by nuclear magnetic resonance spectroscopy.

Preparation C

The anhydride of cis-tetrahydrofuran-2,5-dicarboxylic acid was prepared by adding a solution of dicyclohexylcarbodiimide (1.1 g., 0.0054 mole) in dry diethyl ether (15 ml.) to a solution of said acid (0.81 g., 0.005 mole) in diethyl ether (15 ml.), followed by stirring at room temperature (~25° C.) for a period of ½ hour. After filtering off the precipitate of area which formed, the resulting solution was evaporated under reduced pressure to give tetrahydrofuran-2,5-dicarboxylic anhydride (0.8 g.) as a white solid. The anhydride was used immediately.

EXAMPLE I

Part A

Preparation of 7-[D-$\alpha$-(cis-2-Carboxyoxiran-3-carboxamido)-phenylacetamido]-3-(1-methyl-1,2,3,4-tetrazol-5-ylthiomethyl)-$\Delta^3$-cephem-4-carboxylic Acid.

To a suspension of the trifuoracetic acid addition salt of 7-(D-$\alpha$-aminophenylacetamido)-3-(1-methyl-1,2,3,4- tetrazol-5-ylthiomethyl-Δ³-cephem-4-carboxylic acid (3.5 g., 0.00608 mole) [prepared as described in British Pat. No. 1,283,811 and U.S. Pat. No. 3,641,021] in methylene chloride (100 ml.), there was added triethylamine (2.0 g., 0.020 mole) with vigorous stirring. To the resultant clear solution, there was then added epoxysuccinic anhydride (0.92 g., 0.007 mole) in methylene chloride (10 ml.) and the resulting mixture was stirred for 2 hours at 0° C. The reaction mixture was next washed with aqueous sodium bicarbonate solution, and the aqueous phase was separated and subsequently acidified to pH 2.0 with 2N hydrochloric acid. The suspension so obtained was then extracted with ethyl acetate, the organic phase separated and subsequently dried over anhydrous magnesium sulfate and finally evaporated to dryness while under reduced pressure. In this manner, there were obtained 2.7 g. of a cream solid, which was shown from thin layer chromatography and nuclear magnetic resonance and infra-red spectroscopic data to be 7-[D-α-(cis-2-carboxyoxiran-3-carboxamido)-phenylacetamido]-3-(1-methyl-1,2,3,4-tetrazol-5-ylthiomethyl)-Δ³-cephem-4-carboxylic acid.

Part B

Separation of the Product of Part A into Optical Isomers by High-Pressure Liquid Chromatography.

To the product of Part A of this Example (5.15 mg.), there was added 1.0M sodium acetate solution (0.1 ml., pH 5.5) in one portion. A further amount of sodium acetate solution (0.1 ml.) was then added to give a concentration of approximately 25 μg. of the product per μl. of solution. A 5 μl. sample of this solution was then injected into a Du Pont "830" Liquid Chromatograph, the stainless steel column of which was 0.5 meters long with an internal diameter of 2.1 mm. This instrument was maintained at a temperature of 40° C. and was packed with "Zipax Sax" (a registered trademark name of E.I. duPont de Nemours and Company for a pellicular anion-exchange resin). The pressure above the column was 1500 p.s.i.g. The sample was eluted with pH 5.5 sodium acetate solution at a flow rate of 1.4 ml./minute, the eluent being initially at a concentration of 0.1M, with the concentration of the sodium acetate in the eluent then being steadily increased by 10%/minute to a final value of 1.0 molar. After an initial retention time of 11.60 minutes, one optical isomer eluted and was collected; and after 14.75 minutes, a second isomer subsequently eluted and was likewise collected. Both isomers were found to have anti-bacterial activity.

EXAMPLE II

To a stirred solution of cephalexin (2.0g., 0.0057 mole) in methylene chloride (25 ml.) containing one equivalent (0.8 ml., 0.006 mole) of triethylamine, there was added a solution of monomethylepoxysuccinic anhydride (1.27 g., 0.001 mole) dissolved in 5 ml. of methylene chloride. After about one-half hour, some solid separated out and a further equivalent amount of triethylamine was then added, followed by stirring for 1.5 hours. The resulting solution was then extracted with 10% aqueous sodium bicarbonate solution and the separated aqueous extract thereafter acidified to pH 1.0 with 6N hydrochloric acid. The aqueous acidified phase was next extracted with ethyl acetate, and the separated ethyl acetate phase was subsequently dried over anhydrous magnesium sulfate and filtered, followed by removal of the organic solvent under reduced pressure to afford an oil. The latter oil on trituration with diethyl ether then gave a mixture consisting of 7-[D-α-(cis-2-carboxy-2-methyloxiran-3-carboxamido)-phenylacetamido]-3-desacetoxycephalosporanic acid and 7-[D-α-(cis-2-carboxy-3-methyl-oxiran-3-carboxamido)-phenylacetamido]-3-desacetoxycephalosporanic acid as a yellow solid (0.41 g.), characterized as such by thin layer chromatography and nuclear magnetic resonance and infra-red absorption spectra.

Examples III-XIV

By employing procedures similar to that described in Examples I and II, the following cephalosporan derivatives were prepared from the indicated starting materials, the derivatives being characterized in each instance by thin layer chromatography and nuclear magnetic resonance and infrared absorption spectrosocopy:

| Ex. No. | Starting Materials | Product |
|---|---|---|
| III | epoxysuccinic anhydride and cephaloglycin | 7-[D-α-(cis-2-carboxyoxiran-3-carboxamido)-phenylacetamido]cephalosporanic acid |
| IV | epoxysuccinic anhydride and cephalexin | 7-[D-α-(cis-2-carboxyoxiran-3-carboxamido)-phenylacetamido]-3-desacetoxycephalosporanic acid |
| V | 1,2-epoxycyclohexane-1,2-dicarboxylic acid anhydride and cephaloglycin | 7-[D-α-(cis-1-carboxy-1,2-epoxycyclohexane-2-carboxamido) phenylacetamido]cephalosporanic acid |
| VI | 1,2-epoxycyclohexane-1,2-dicarboxylic acid anhydride and cephalexin | 7-[D-α-(cis-1-carboxy-1,2-epoxycyclohexane-2-carboxamido)phenylacetamido]-3-desacetoxycephalosporanic acid |
| VII | tetrahydrofuran-2,5-dicarboxylic acid anhydride and cephaloglycin | 7-[Dα-(cis-2-carboxytetrahydrofuran-5-carboxamido)phenylacetamido]cephalosporanic acid |
| VIII | tetrahydrofuran-2,5-dicarboxylic acid anhydride and cephalexin | 7-[D-α-(cis-2-carboxytetrahydrofuran-5-carboxamido)phenylacetamido]-3-desacetoxycephalosporanic acid |
| IX | 2,5-dihydrofuran-2,5-dicarboxylic acid anhydride and cephalexin | 7-[D-α-(cis-2-carboxy-2,5-dihydrofuran-5-carboxamido)phenylacetamido]-3-desacetoxycephalosporanic acid |
| X | 2,5-dihydrofuran-2,5-dicarboxylic acid anhydride and cephaloglycin | 7-[D-α-(cis-2-carboxy-2,5-dihydrofuran-5-carboxamido)phenylacetamido]cephalosporanic acid |
| XI | monomethylepoxysuccinic anhydride and cephaloglycin | Mixture of 7-[D-α-(cis-2-carboxy-2-methyl-oxiran-3-carboxamido)phenylacetamido]-cephalosporanic acid and 7-[D-α-(cis-2-carboxy-3-methyloxiran-3-carboxamido)-phenylacetamido]cephalosporanic acid |
| XII | monomethylepoxysuccinic anhydride and the trifluoracetic acid salt of 7-[D-α-aminophenylacetamido)-3-(1-methyl-1,2,3,4-tetrazol-5-ylthio)-Δ³-cephem-4-carboxylic acid | Mixture of 7-[D-α-(cis-2-carboxy-2-methyl-oxiran-3-carboxamido)phenylacetamido]-3-(1-methyl-1,2,3,4-tetrazol-5-ylthio)-Δ³-cephem-4-carboxylic acid and 7-[D-α-(cis-2-carboxy-3-methyloxiran-3-carboxamido)- |

Examples III-XIV-continued

By employing procedures similar to that described in Examples I and II, the following cephalosporan derivatives were prepared from the indicated starting materials, the derivatives being characterized in each instance by thin layer chromatography and nuclear magnetic resonance and infrared absorption spectrosocopy:

| Ex. No. | Starting Materials | Product |
|---|---|---|
| | | phenylacetamido]-3-(1-methyl-1,2,3,4-tetrazol-5-ylthio)-Δ³-cephem-4-carboxylic acid |
| XIII | dimethylepoxysuccinic anhydride and cephalexin | 7-[D-α-(cis-2-carboxy-2,3-dimethyloxiran-3-carboxamido)phenylacetamido]-3-desacetoxycephalospiranic acid |
| XIV | dimethylepoxysuccinic anhydride and cephaloglycin | 7-[D-α-(cis-2-carboxy-2,3-dimethyloxiran-3-carboxamido)phenylacetamido]cephalosporanic acid |

EXAMPLE XV

Epoxysuccinic anhydride (1.14 g.) was dissolved in diethyl ether (10 ml.) and to the resulting solution, there was then added a solution of 2-methoxyphenol (1.24 g., 0.01 mole) in diethyl ether (5 ml.), followed by triethylamine (1.01 g., 0.01 mole). An oil soon separated out and dry methylene chloride was added to the reaction mixture until a clear solution was obtained, followed by stirring for a period of one-half hour. The solvent was then evaporated under reduced pressure to afford a pale-brown solid, which was subsequently recrystallized from water. The recrystallized solid (0.71 g.), viz., mono(2-methoxyphenyl) cis-epoxysuccinate, had a melting point of 167°–169° C. and was characterized by nuclear magnetic resonance and infrared absorption spectroscopy.

The thus-produced mono-ester (0.6 g., 0.0025 mole) was next reacted at room temperature (~25° C.) with N-hydroxysuccinimide (0.29 g., 0.0025 mole) and dicyclohexylcarbodiimide (0.52 g., 0.0025 mole) in dry methylene chloride (10 ml.) to yield a solution of the N-succinimido ester of 2-methoxyphenyl cisepoxysuccinate. The activated half-ester was then coupled (while still in solution) with cephaloglycin in the presence of triethylamine according to the procedure of Examples I—II to ultimately afford pure 7-{D-α-[cis-2-(2-methoxyphenoxycarbonyl)-oxiran-3-carboxamido]-phenylacetamido}-cephalosporanic acid as the desired final product.

EXAMPLE XVI

The following 7-D-α-acylaminophenylacetamido)-Δ³-cephem derivatives are prepared by employing the procedures described in Example I, starting from the corresponding 7-(D-α-aminophenylacetamido)-3-substituted-Δ³-cephem-4-carboxylic acid and appropriate anhydride in each instance:

7-[D-α-(cis-2-carboxyoxiran-3-carboxamido)-phenylacetamido]-3-(pyrmidin-2-ylthiomethyl)-Δ³-cephem-4-carboxylic acid 7-[D-α-(cis-2-carboxyoxiran-3-carboxamido)-phenylacetamido]-3-(4,6-diemthylpyrimidin-2-ylthiomethyl)-Δ³-cephem-4-carboxylic acid 7-[D-α-(cis-2-carboxy-2,3-dimethyloxiran-3-carboxamido)-phenylacetamido]-3-(4,5-dimethylthiazol-2-ylthiomethyl)-Δ³-cephem-4-carboxylic acid 7-[D-α-(cis-2-carboxyoxiran-3-carboxamido)-phenylacetamido]-3-(1,3,5-triazin-2-ylthiomethyl)-Δ³-cephem-4-carboxylic acid 7-[D-α-(cis-2-carboxyoxiran-3-carboxamido)-phenylacetamido]-3-(2-methyl-1,3,4-thiadiazol-5-ylthio)-Δ³-cephem-4-carboxylic acid 7-[D-α-(cis-2-carboxyoxiran-3-carboxamido)-phenylacetamido]-3-(2-methyl-1,3,4-oxadiazol-5-ylthiomethyl)-Δ³-cephem-4-carboxylic acid 7-[D-α-(cis-2-carboxyoxiran-3-carboxamido)-phenylacetamido]-3-(1-benzyl-1,2,3,4-tetrazol-5-ylthiomethyl)-Δ³-cephem-4-carboxylic acid 7-[D-α-(cis-2-carboxy-2,3-dimethyloxiran-3-carboxamido)-phenylacetamido]-3-(1-phenyl-1,2,3,4-tetrazol-5-ylthiomethyl)-Δ³-cephem-4-carboxylic acid 7-[D-α-(cis-2-carboxyoxiran-3-carboxamido)-phenylacetamido]-3-[1-(4-chlorophenyl)-1,2,3,4-tetrazol-5-ylthiomethyl]-Δ³-cephem-4-carboxylic acid 7-[D-α-(cis-2-carboxyoxiran-3-carboxamido)-phenylacetamido]-3-[1-(4-anisyl)-1,2,3,4-tetrazol-5-ylthiomethyl]-Δ³-cephem-4-carboxylic acid.

EXAMPLE XVII

The following 7-(D-α-acylaminoarylacetamido)-Δ³-cephem derivatives (where 1-MT-5-YLS represents the 1-methyl-1,2,3,4-tetrazol-5-ylthio group in the table) are prepared by employing the procedures described in the previous Examples, starting from the corresponding 7-(α-aminoarylacetamido)-Δ³-cephem derivative and the appropriate cyclic anhydride or "activated" half-ester reagent as the case may be:

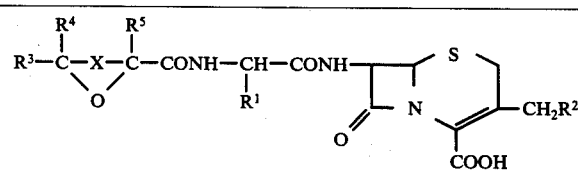

| R¹ | R² | R³ | R⁴ | R⁵ | X |
|---|---|---|---|---|---|
| 4-HOC₆H₄ | H | COOH | H | H | direct link |
| 3-Cl-4-HOC₆H₃ | H | COOH | H | H | direct link |
| 4-HOC₆H₄ | OCOCH₃ | COOH | H | H | direct link |
| 3-Cl-4-HOC₆H₃ | OCOCH₃ | COOH | H | H | direct link |

-continued

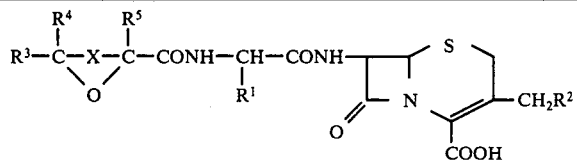

| R¹ | R² | R³ | R⁴ | R⁵ | X |
|---|---|---|---|---|---|
| 4-HOC₆H₄ | 1-MT-5-YLS | COOH | H | H | direct link |
| 3-Cl-4-HOC₆H₃ | 1-MT-5-YLS | COOH | H | H | direct link |
| 4-Cl-C₆H₄ | H | COOH | H | H | —(CH₂)₂— |
| 4-CH₃H₄ | H | COOH | H | H | —(CH₂)₂— |
| 4-CF₃C₆H₄ | OCOCH₃ | COOH | CH₃ | CH₃ | direct link |
| 2-thienyl | OCOCH₃ | COOCH₃ | H | H | direct link |
| 3-thienyl | 1-MT-5-YLS | COOH | H | H | direct link |
| 2-furyl | OCOCH₃ | COOH | H | H | direct link |
| 3-BrC₆H₃ | OCOCH₃ | COOH | H | H | direct link |
| C₆H₅ | 1-MT-5-YLS | COOH | CH₃ | CH₃ | direct link |
| C₆H₅ | 1-MT-5-YLS | COOH | CH₃ | H | direct link |
| C₆H₅ | 1-MT-5-YLS | COOH | —(CH₂)₄— | | direct link |
| C₆H₅ | OCOCH₃ | COOC₂H₅ | —(CH₂)₃— | | direct link |
| C₆H₅ | 1-MT-5-YLS | COOH | H | H | —(CH₂)₂— |
| C₆H₅ | H | COOH | H | H | —(CH₂)₃— |
| C₆H₅ | 1-MT-5-YLS | COOH | H | H | —CH=CH— |
| C₆H₅ | 1-MT-5-YLS | COOC₆H₅ | H | H | direct link |
| C₆H₅ | H | COOC₁₀H₇(α-) | H | H | direct link |
| C₆H₅ | H | CON(C₂H₅)₂ | H | H | direct link |
| 4-FC₆H₄ | H | COOH | CH₃ | CH₃ | direct link |
| 3-IC₆H₄ | OCOCH₃ | COOH | H | H | direct link |
| 2-CH₃OC₆H₄ | H | COOH | H | H | —(CH₂)₂— |
| 2-thienyl | OCOCH₃ | COOC₆H₅ | H | H | direct link |
| C₆H₅ | H | COOC₉H₉(5-) | H | H | direct link |
| C₆H₅ | N₃ | COOH | H | H | direct link |
| C₆H₅ | OCONH₂ | COOH | H | H | direct link |

EXAMPLE XVIII

The sodium salt of 7-[D-α-(cis-2-Carboxyoxiran-3-carboxamido)-phenylacetamido]-3-(1-methyl-1,2,3,4-tetrazol-5-ylthiomethyl)-Δ³-cephem-4-carboxylic acid is prepared by dissolving said acid in water containing an equivalent amount of moles of sodium hydroxide and then freeze-drying the mixture. In this way, the desired alkali metal salt of the acid is obtained in the form of an amorphous powder which is freely soluble in water.

In like manner, the potassium and lithium salts are also similarly prepared, as are the alkali metal salts of all the other acidic 7-(D-α-acylaminoarylacetamido)-Δ³-cephem derivatives of this invention which are reported in Examples II-XVII, respectively.

EXAMPLE XIX

The calcium salt of 7-[D-α-(cis-2-carboxyoxiran-3-carboxamido)-phenylacetamido]cephalosporanic acid is prepared by dissolving said acid in water containing an equivalent amount in moles of calcium hydroxide and then freeze-drying the mixture. The corresponding magnesium salt is also prepared in like manner, as are all the other alkaline-earth metal salts not only of this particular compound, but also of those acids previously described in Examples I-II and IV-XVII, respectively.

What is claimed is:

1. A compound of the formula:

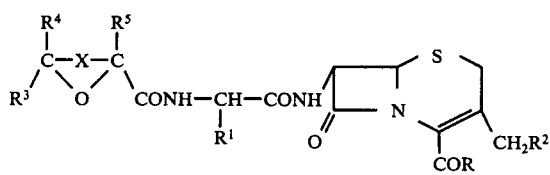

and the pharmaceutically acceptable base salts thereof, wherein

R¹ is a member selected from the group consisting of phenyl, thienyl and 2-furyl, and mono substituted phenyl wherein the substituent is chosen from the group consisting of halogen, hydroxy, lower alkyl, lower alkoxy and trifluoromethyl;

R is hydroxy, and R² is a member selected from the group consisting of pyrimidin-2-ylthio, 4,6-dimethylpyrimidin-2-ylthio, 4,5-dimethylthiazol-2-ylthio, 1,3,5-triazin-2-ylthio, 2-methyl-1,3,4-thiadiazol-5-ylthio, 2-methyl-1,3,4-oxadiazol-5-ylthio and 1-substituted-1,2,3,4-tetrazol-5-ylthio wherein the 1-substituent is chosen from the group consisting of lower alkyl, benzyl, phenyl, chlorophenyl and anisyl;

R³ is a member selected from the group consisting of carboxy, COOR⁶ wherein R⁶ is chosen from the group consisting of lower alkyl, 5-indanyl, naphthyl, phenyl and mono substituted phenyl wherein the substituent is chosen from the group consisting of halogen, lower alkyl, lower alkoxy and trifluoromethyl, and CONR⁷R⁸ wherein R⁷ and R⁸ are each chosen from the group consisting of hydrogen, lower alkyl and cycloalkyl having from three to six carbon atoms;

R⁴ and R⁵ are each a member selected from the group consisting of hydrogen and lower alkyl, and X is a direct carbon-carbon link.

2. A compound as claimed in claim 1 wherein R is hydroxy and R¹ is phenyl.

3. A compound as claimed in claim 1 wherein R is hydroxy, R¹ is phenyl and R³ is COOR⁶ wherein R⁶ is lower alkoxyphenyl.

4. A compound as claimed in claim 1 wherein R is hydroxy, R¹ is phenyl and R³ is carboxy.

5. A compound as claimed in claim 1 wherein R is hydroxy, R¹ is phenyl, R³ is carboxy, and R⁴ and R⁵ are each hydrogen or methyl.

6. A compound as claimed in claim 1 wherein R is hydroxy, $R^1$ is phenyl, $R^2$ is 1-(lower alkyl)-1,2,3,4-tetrazol-5-ylthio, $R^3$ is carboxy, and $R^4$ and $R^5$ are each hydrogen or methyl.

7. A compound as claimed in claim 6 wherein $R^2$ is 1-methyl-1,2,3,4-tetrazol-5-ylthio.

8. 7-[D-α-(cis-2-Carboxyoxiran-3-carboxamido)-phenylacetamido]-3-(1-methyl-1,2,3,4-tetrazol-5-ylthiomethyl)-Δ³-cephem-4-carboxylic acid.

9. An antibacterial pharmaceutical composition comprising a compound as claimed in claim 1 and a pharmaceutically acceptable carrier.

10. A method for treating an animal of diseases caused by Gram-negative and Gram-positive bacteria, which comprises administering to said animal an antibacterially-effective amount of a compound as claimed in claim 1.

* * * * *